United States Patent [19]
Rummel

[11] Patent Number: 4,602,870
[45] Date of Patent: Jul. 29, 1986

[54] METHOD AND APPARATUS FOR DETERMINING THE PRESENCE OR ABSENCE OF A POUR POINT DEPRESSANT ADDITIVE IN HYDROCARBON LIQUIDS

[75] Inventor: Jon D. Rummel, Broken Arrow, Okla.

[73] Assignee: Citgo Petroleum Corporation, Tulsa, Okla.

[21] Appl. No.: 652,617

[22] Filed: Sep. 20, 1984

Related U.S. Application Data

[63] Continuation-in-part of Ser. No. 430,539, Sep. 30, 1982, abandoned.

[51] Int. Cl.⁴ ............................................. G01N 25/02
[52] U.S. Cl. ...................................... 374/16; 374/19; 374/20
[58] Field of Search ..................... 374/16, 25, 19, 17, 374/26; 73/64

[56] References Cited

U.S. PATENT DOCUMENTS

| | | | |
|---|---|---|---|
| 3,031,880 | 5/1962 | Findlay | 374/17 |
| 3,187,557 | 6/1965 | Holbourne | 374/19 |
| 3,248,928 | 5/1966 | Conklin et al. | 73/64 |
| 3,447,358 | 6/1969 | Crespin et al. | 374/16 |
| 3,457,772 | 7/1969 | Chassagne et al. | 374/17 |
| 3,545,254 | 2/1968 | Chassagne et al. | 374/17 |
| 3,667,280 | 6/1972 | Simpson | 374/25 |
| 3,677,064 | 7/1972 | Simpson | 374/25 |
| 4,008,604 | 2/1977 | Roach et al. | 374/26 |
| 4,443,118 | 4/1984 | Cure | 374/26 |
| 4,508,460 | 4/1985 | Croo | 374/16 |

*Primary Examiner*—Charles Frankfort
*Assistant Examiner*—David R. Schuster
*Attorney, Agent, or Firm*—Cushman, Darby & Cushman

[57] ABSTRACT

A method and apparatus for determining the presence or absence of a pour point depressant additive in hydrocarbon liquids includes cooling a sample of the liquid at a predetermined cooling rate from a temperature substantially above the cloud point temperature of the sample liquid to a temperature substantially below the cloud point temperature of the sample liquid. The points on the cooling rate curve for the sample at which a deflection of the curve begins and ends is determined and the time interval between the beginning and ending points of the cooling rate curve is computed. This computed time interval between the beginning and ending points is compared to a reference time interval such that if the reference time interval is less than or greater than the computed time interval between the beginning and ending points on the cooling curve, the presence or absence, respectively, of a pour point depressant additive in the sample is determined.

11 Claims, 3 Drawing Figures

METHOD AND APPARATUS FOR DETERMINING THE PRESENCE OR ABSENCE OF A POUR POINT DEPRESSANT ADDITIVE IN HYDROCARBON LIQUIDS

CROSS-REFERENCE TO RELATED APPLICATIONS

This application is a continuation-in-part of copending U.S. application Ser. No. 430,539 filed Sept. 30, 1982, now abandoned, the entire disclosure thereof being expressly incorporated hereinto by reference.

BACKGROUND AND SUMMARY OF THE INVENTION

The present invention relates to a method and apparatus for determining the presence or absence of a pour point depressant additive, also known as a wax crystal modifier and a flow improver additive, in hydrocarbon liquids derived from petroleum. The present invention relates to the novel discovery that the time-duration of a plateau for a hydrocarbon liquid cooling curve is indicative of the presence or absence of a pour point depressant. Thus, the presence or absence of a pour point depressant in samples of hydrocarbon liquids can now be readily identified.

The cloud point temperature of a hydrocarbon liquid derived from petroleum is a wellrecognized term in the petroleum industry and is further defined by ASTMD 2500, Standard Test Method for Cloud Point of Petroleum Oils. There has thus previously been references relating to cloud point determinations such as U.S. Pat. Nos. 3,031,880, 3,187,557, 3,457,772 and 3,545,254. Each of these references generally measure the cloud point temperature by measuring light passing through a sample while the sample is being cooled.

U.S. Pat. No. 3,447,358 cools a sample in such a way that convection currents are generated in the sample. At the cloud point, a crystal lattice formation reduces or stops the convection currents and this lowering or cessation of currents can be measured optically, mechanically, or acoustically.

Thus, it is known in the art that the cloud point temperature of an oil can be determined from a cooling curve (temperature versus time) of a hydrocarbon liquid sample which is based upon a theory that at the moment when, during the cooling, paraffin wax starts to crystallize out, the latent heat evolved in the crystallization process will retard the cooling of the hydrocarbon liquid. Thus, the cooling curve will show a substantially constant temperature plateau at the point where crystallization of the paraffin wax begins, and the temperature corresponding to this plateau is, at least approximately, the cloud point temperature of the hydrocarbon liquid.

The present invention utilizes the cloud point temperature as the beginning point for determining the presence or absence of a pour point depressant in the hydrocarbon liquid sample. Thus, the present invention relates to first determining the beginning point of the plateau in a temperature versus time cooling curve of a sample and then subsequently determining the ending point for the plateau. It has been discovered that the time interval between the beginning and ending points of a hydrocarbon liquid cooling curve establishes the presence or absence of a pour point depressant additive in the sample liquid when compared to a reference time interval. It has thus been discovered that a reference time interval of about 3.5 minutes is valid over a substantially wide range of cooling rates (e.g. 6° C./hr. to 20° C./hr.) and thus if a measured time interval for the temperature plateau on a cooling rate curve for a hydrocarbon liquid sample is less than or greater than the 3.5 minute reference time interval, the presence or absence respectively, of a pour point depressant additive is confirmed.

Accordingly, the present invention contemplates that a sample of a hydrocarbon liquid is cooled from a temperature substantially above the cloud point temperature to a temperature substantially below the cloud point. The slope of the cooling rate curve is monitored and the points at which a deflection in the curve begins and ends is monitored. The beginning and ending deflections are thus indicative of the beginning and ending of a plateau on the temperature versus time cooling curve of the sample. The time interval between the beginning and ending deflections of the curve are thus determined and this determined time interval is compared to a reference time interval so as to establish the presence or absence of a pour point depressant additive.

Accordingly, the present invention provides a method and apparatus whereby the presence or absence of a pour point depressant additive can be readily determined in a sample hydrocarbon liquid.

BRIEF DESCRIPTION OF THE ACCOMPANYING DRAWINGS

Reference will be hereinafter made to the accompanying drawings where in like reference numerals throughout the various figures denote like structural features and wherein.

Figure 1:
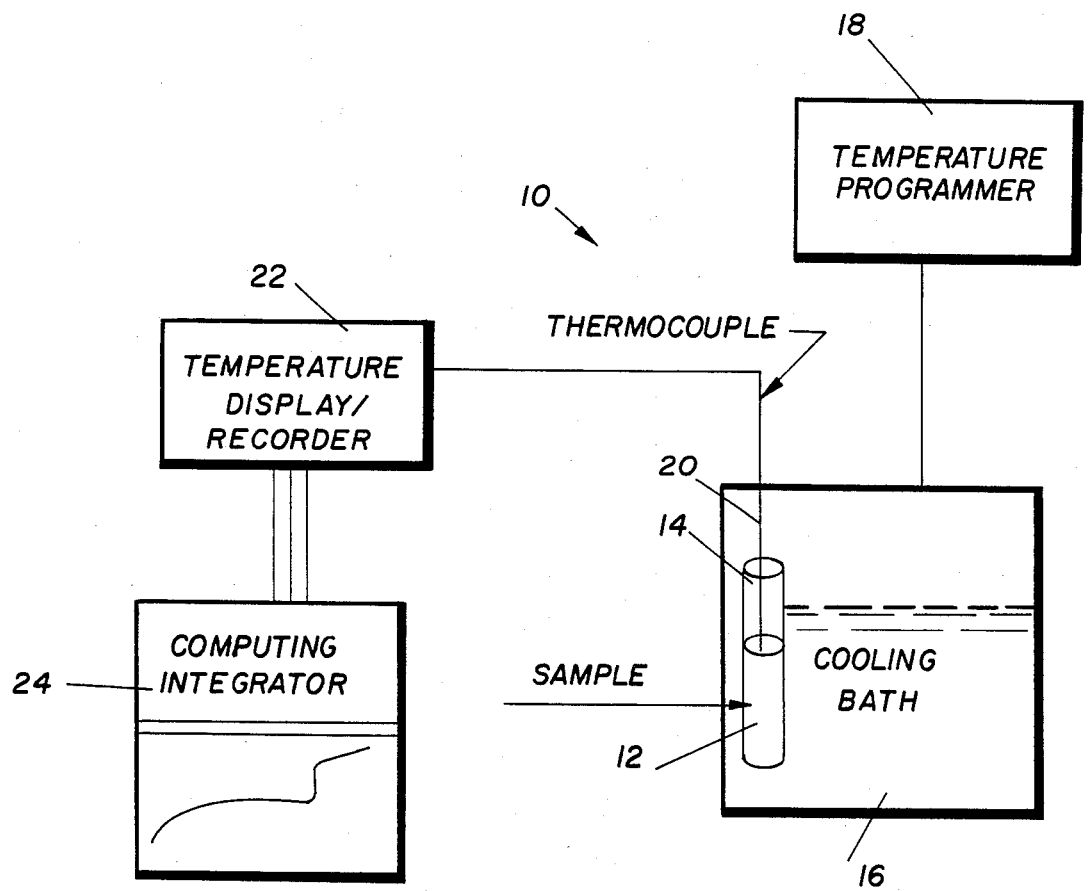
FIG. 1 is a schematic representation of an apparatus of the present invention used to determine the presence or absence of a pour point additive in a hydrocarbon liquid sample.

DETAILED DESCRIPTION OF THE PREFERRED EXAMPLE EMBODIMENT IN ACCORDANCE WITH THE PRESENT INVENTION

A hydrocarbon liquid derived from petroleum is the material to be tested in accordance with this invention. I broadly define this hydrocarbon liquid derived from petroleum as defined by ASTM standard fuel oil grades Nos. 1, 1-D, 2, 2-D, 4, 5 and 6 as specified by ASTM D396, diesel fuel of grades No. 1-D, No. 2-D and No. 4-D as specified by ASTM D975, aviation turbine fuel as specified by ASTM D1655, as well as motor oils defined as having the characteristics of SAE 5W through SAE 50. Engine oils are classified by grades based on their viscosity as prescribed by SAE Recommended Practice SAE J 300D. Hydrocarbon liquids also include lubricants used for industrial purposes such as hydraulic oils and gear lubricants. The definition of the hydrocarbon also includes any unfinished blend streams from petroleum refineries that are later processed or combined to give the materials covered by the above definitions. Examples of some of the various hydrocarbon liquids covered by this definition are kerosene, fuel oils, diesel fuels, components of these finished products which include atmospheric gas oils, catalytic cracker recycle oil, vacuum gas oils and other distillate fractions for fuels, and components for lubricants such as neutral oils and bright stocks. These streams typically contain varying amounts of paraffin wax, and the determination of this amount of wax is important in determining the specifications and performance of the finished products containing these various liquids. Table I below show the paraffin distribution in assorted fuels.

TABLE I

N—PARAFFIN DISTRIBUTION IN ASSORTED FUELS
N—paraffin Content, wt. %

| Carbon Chain Length | 21 | 22 | 23 | 24 | 25 | 26 | 27 | 28 |
|---|---|---|---|---|---|---|---|---|
| 7 | Trace | Trace | — | .01 | Trace | .01 | Trace | — |
| 8 | .42 | .03 | .04 | .46 | .02 | .03 | .02 | .01 |
| 9 | .67 | .11 | .10 | .69 | .10 | .10 | .08 | .07 |
| 10 | .92 | .42 | .34 | .91 | .41 | .42 | .41 | .34 |
| 11 | 1.09 | .83 | 1.04 | 1.08 | .83 | .84 | .85 | 1.08 |
| 12 | 1.37 | 1.10 | 2.29 | 1.33 | 1.08 | 1.10 | 1.09 | 2.36 |
| 13 | 2.05 | 1.31 | 3.03 | 1.61 | 1.31 | 1.31 | 1.30 | 3.08 |
| 14 | 2.23 | 1.24 | 3.09 | 2.18 | 1.24 | 1.25 | 1.21 | 3.16 |
| 15 | 3.70 | 1.56 | 3.19 | 3.73 | 1.58 | 1.59 | 1.54 | 3.25 |
| 16 | 3.32 | 1.65 | 2.96 | 3.31 | 1.66 | 1.64 | 1.63 | 3.02 |
| 17 | 1.25 | 1.41 | 2.79 | 1.25 | 1.42 | 1.40 | 1.42 | 2.84 |
| 18 | .52 | 1.02 | 2.19 | .52 | 1.02 | 1.01 | 1.03 | 2.23 |
| 19 | .44 | .97 | 2.03 | .56 | .97 | .97 | .97 | 2.07 |
| 20 | .44 | .62 | 1.55 | .43 | .61 | .61 | .60 | 1.57 |
| 21 | .36 | .49 | 1.16 | .36 | .48 | .49 | .48 | 1.19 |
| 22 | .19 | .33 | .69 | .27 | .31 | .31 | .30 | .71 |
| 23 | .12 | .22 | .40 | .13 | .21 | .23 | .21 | .42 |
| 24 | .06 | .15 | .22 | .05 | .14 | .15 | .14 | .23 |
| 25 | .02 | .10 | .12 | .02 | .10 | .10 | .10 | .13 |
| 26 | .01 | .05 | .06 | .01 | .05 | .05 | .05 | .06 |
| 27 | Trace | .03 | .03 | Trace | .03 | .03 | .03 | .03 |
| 28 | Trace | .01 | .01 | — | .01 | .01 | .01 | .01 |
| 29 | — | .01 | Trace | — | Trace | Trace | Trace | Trace |
| 30 | — | Trace | — | — | Trace | Trace | Trace | Trace |

The apparatus 10 preferably used in the determination of the presence or absence of a pour point depressant additive in hydrocarbon liquid samples is schematically shown in accompanying FIG. 1. As shown therein, a hydrocarbon liquid sample 12 housed in a suitable container 14 is immersed in a liquid cooling bath 16. The cooling bath 16 is cooled at a substantially constant rate by means of a conventional temperature programmer 18. A thermocouple 20 is immersed in the sample 12 and is connected to a temperature display 22. The cooling bath 16 thus cools sample 12 at a substantially constant rate and this constant rate cooling is sensed by thermocouple 20 and transmitted to temperature display/recorder 22 (e.g. such as a strip chart recorder) to visually display and record the temperature curve of the sample. A computing integrater 24 is operably coupled to the temperature display 22 and thus to the thermocouple 20.

A typical procedure for determining the presence or absence of a pour point depressant additive involves placing a sample 12 in a cooling bath 16. The sample 12, in a convenient container 14, has a thermocouple 20 centrally located in the sample and leading to a computing integrator device 24. The temperature of the cooling bath 16 is lowered at a regular and predetermined rate and the temperature of the sample 12 is suitably determined by the computing integrator device 24 as will be discussed in greater detail below. The cooling rate of sample 12 can vary from about 6° C. to about 20° C./hr. The rate of cooling of the bath 16 is linear and is reflected by the cooling rate curve sensed by the device 24.

Figure 2:
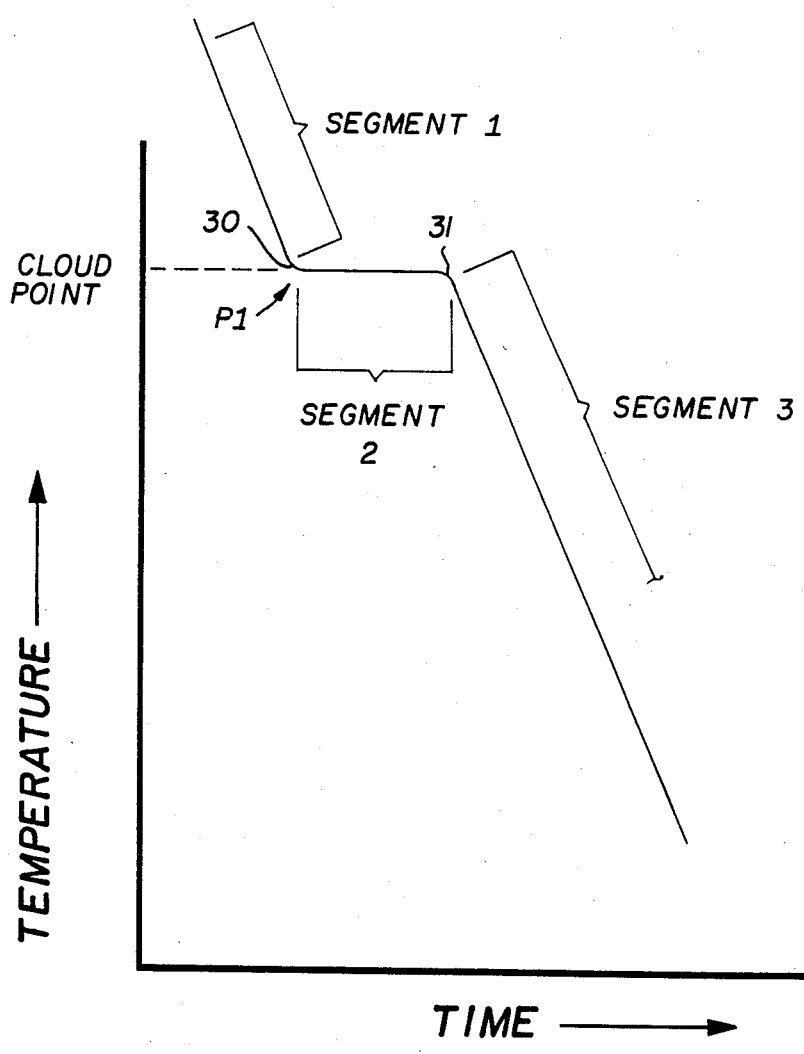
FIG. 2 is a representative temperature versus time cooling rate curve for hydrocarbon liquid samples.

At some point in the temperature curve, the paraffin wax experiences a change of state from liquid to solid and begins to crystallize from the hydrocarbon liquid. This latent heat of crystallization causes a change in the cooling rate curve, this change being known as a deflection point Pl as shown in FIG. 2. A typical cooling curve will display three distinct segments i.e., (1) from the beginning of the cooling period to the beginning of the deflection of the curve (noted as "Segment 1" in FIG. 2); (2) from the beginning of the deflection to its end (noted as "Segment 2" in FIG. 2; and (3) from the end of the deflection to the end of the cooling period (noted as "Segment 3" in FIG. 2).

After the wax in the sample solidifies, the cooling rate curve generally resumes its downward slope. e.g. identified as Segment 3 in FIG. 2. The beginning deflection point 30 of the cooling curve is usually abrupt or sharp. When the cooling rate curve continues after the beginning deflection point 30, the presence or absence of a pour point depressant additive can be determined by the length of time required for the cooling curve to resume its downward slop after its ending deflection point 31. That is, the time interval of Segment 2 (the cooling curve plateau) is indicative of the presence or absence of a pour point depressant additive when compared to a reference time interval of 3.5 minutes, for example.

Figure 3:
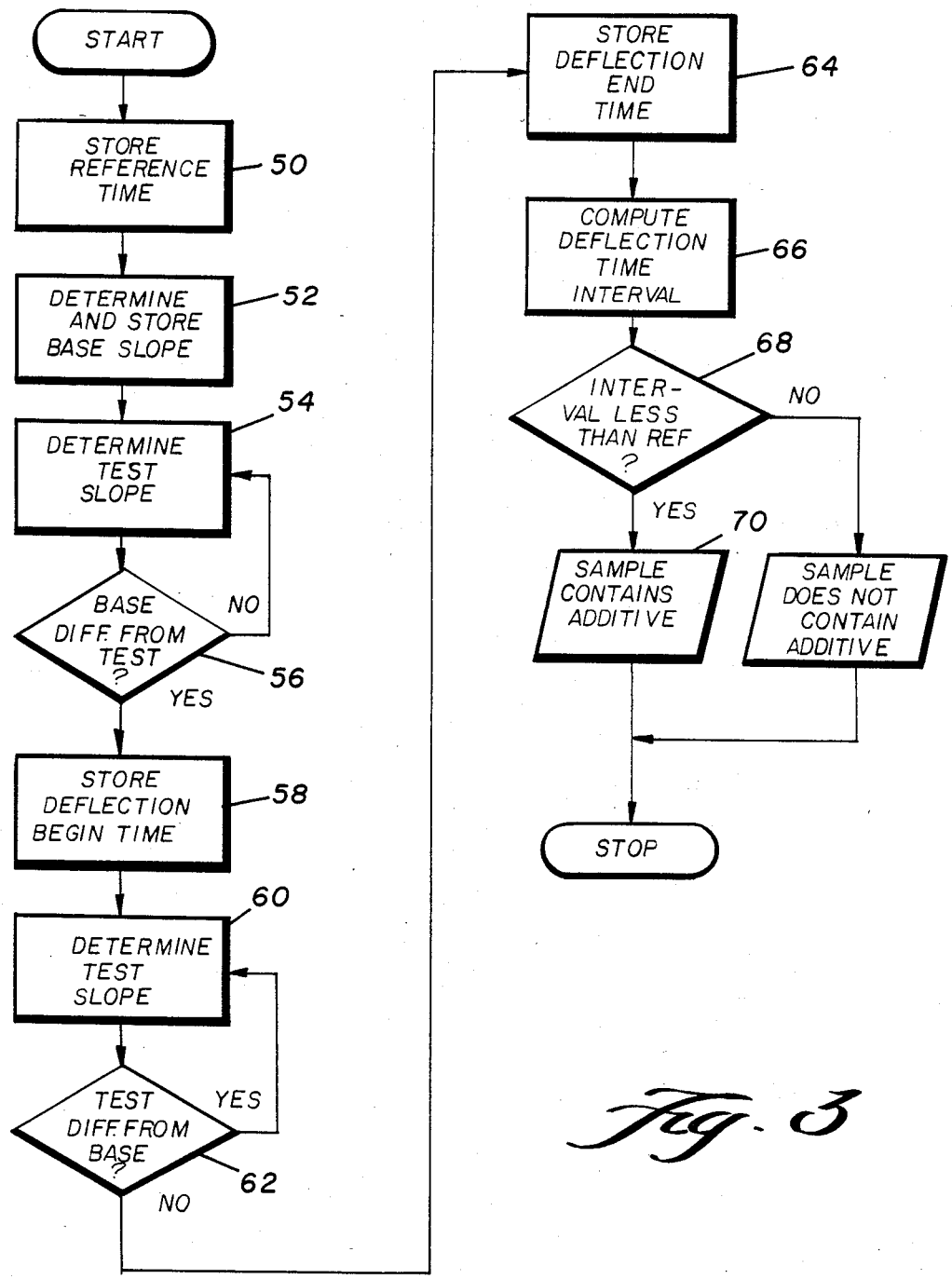
FIG. 3 is a logic diagram for automatically determining the presence or absence of a pour point depressant additive.

The computing integrator 24 is programmed so as to execute the steps indicated in accompanying FIG. 3. As shown therein, a reference temperature of 3.5 minutes is first stored into memory in a step 50. A base slope of the cooling rate curve of sample 12 is then determined in step 52 by obtaining temperature/ time relationships between about 5.0 and 8.0 minutes after the execution of the program. The base slope of the cooling curve will thereby establish a reference slope for further slope determinations. A test slope is then determined in step 54 at every 0.01 minutes. For example, during the cooling rate determination, the test slope is then compared in step 56 to the base slope determined in step 52. If the slope comparison performed in step 56 indicates that the test slope is different from the base slope, an indication is thus present that deflection of the cooling curve has begun (e.g. crystallization of the paraffin wax at the cloud point temperature has begun). Thus, a deflection begin time is stored in step 58. If the base slope is not different from the test slope, further test slopes are determined and the comparison between the test slope and the base slope is repeated in step 56.

Once a beginning curve deflection has been sensed, further test slopes are determined in step 60 as was the case in step 54 and a comparison is again made in step 62 to determine if there is again any difference between the test and base slopes. If there is no difference between the test and base slopes, an indication is present that the plateau of the cooling curve has terminated and that the downward curve of the slope has thus begun. Accordingly, in step 64, the deflection end time corresponding to the deflection ending point is stored. The time interval between the deflection begin and end times is determined in step 66 by subtracting the deflection begin time from the deflection end time. The thus determined time interval is compared in step 68 to the 3.5 reference time interval previously stored in step 50. In step 70, if the reference time is greater than the time interval of the plateau determined in step 66, device 24 will automatically print that the sample contains a pour point depressant additive whereas if the reference time is less than the time interval, the device 24 will print that the sample does not contain the pour point depressant additive.

Thus, in accordance with the present invention, automatic means are provided whereby a determination can be made if a sample hydrocarbon liquid contains a pour point depressant additive. That is, samples with additives require less than about 3.5 minutes to reestablish the cooling curve while samples which do not contain additives require greater than about 3.5 minutes to establish the downward slope of the cooling curve. Within the cooling rates investigated (i.e. 6° C./hr. to 20° C./hr.), the time of about 3.5 minutes remains valid.

Table II below is a tabulation of data associated with the present invention. A variety of hydrocarbon liquids derived from petroleum, cooling rates, cloud points, and deflection times were investigated and noted. Some of the samples incorporated typical pour point depressant additives, such as ethlyene-vinylacetate copolymers, at levels varying from 157 to 753 ppm. For example, sample B' has the same petroleum liquid base as does sample B with the exception that sample B' includes a pour point depressant additive.

presently known method or apparatus is available which determines the presence or absence of a pour point depressant based upon a comparison to a reference time interval which has herein been discovered as being indicative of the presence or absence of a pour point depressant.

Accordingly, while the present invention has been herein described in was presently conceived to be the most preferred embodiments thereof, those in this art may recognize that many modifications may be made hereof which modifications shall be accorded the broadest scope of the appended claims so as to encompass all equivalent methods, processes, and systems.

What is claimed is:

1. A method of determining the presence or absence of a pour point depressant additive in a hydrocarbon liquid derived from petroleum, said liquid containing paraffin wax, comprising the steps of:
    (a) cooling a sample of said liquid at a predetermined cooling rate from a temperature substantially above the cloud point temperature to a temperature substantially below the cloud point temperature;
    (b) monitoring the slope of the cooling rate curve and noting the points at which a deflection in the curve begins and ends;
    (c) determining the time interval between the beginning and ending points of the deflection of the curve, and
    (d) comparing the determined time interval to a reference time interval, associated with said predetermined cooling rate, so as to establish whether the determined time interval is less than or greater than the reference time interval thereby establishing the presence or absence, respectively, of a pour point depressant additive.

2. The method of claim 1 wherein:
    (a) the rate at which the sample is cooled varies from about 6° C. to about 20° C./hr; and
    (b) the presence of a pour point depressant additive is noted when the duration time of the deflection curve is less than about 3.5 minutes.

3. A method of determining the presence or absence of a pour point depressant additive in a hydrocarbon liquid comprising the steps of:
    (a) cooling a sample of the hydrocarbon liquid at a predetermined cooling rate from a temperature substantially above the cloud point temperature of the sample liquid to a temperature substantially

TABLE II

| | | | ASSORTED CLOUD POINT DETERMINATIONS | | |
|---|---|---|---|---|---|
| Product Type | Sample | Cooling Rate (°C./hr) | Cloud Point (°C.) By the Invention | Cloud Point (°C.) By ASTM D-2500 | Deflection Time (Min.) |
| Aviation Turbine Fuel | A | 8 | −48.2 | −44 | 12.0 |
| Diesel Fuel | B | 10 | −9.2 | −9 | 10.0 |
| B + Additive | B' | 15 | −11.2 | −9 | 1.5 |
| | C | 10 | −20.6 | −19 | 4.5 |
| Lubricant Base Stock | D | 20 | −11.6 | −14 | 5.0 |
| Fuel Oil | E | 15 | −13.4 | −14 | 8.5 |
| | F | 15 | −13.2 | −10 | 2.0 |
| | G | 15 | −7.9 | −8 | 7.0 |
| G + Additive | G' | 15 | −8.9 | −9 | 1.5 |
| G + Additive | G" | 6 | −8.6 | −9 | 2.0 |
| Industrial Lubricant | H | 20 | −15.5 | −16 | 8.0 |

As the reader will now undoubtedly appreciate, the present invention provides distinct advantages in determining whether or not a hydrocarbon liquid sample includes pour point liquid depressant additives. No below the cloud point temperature of the sample liquid;
    (b) continously sensing the temperature of the sample liquid while the sample liquid is cooled according to step (a) to establish a cooling rate curve for the sample liquid;

(c) determining points on the cooling rate curve at which a deflection of the curve begins and ends;

(d) determining the time interval between the beginning and ending points of the cooling rate curve deflection; and (e) comparing the determined time interval with a reference time interval associated with said predetermined cooling rate to establish whether the determined time interval is less than or greater than the reference time interval to respectively establish the presence or absence of a pour point depressant additive in the sample liquid.

4. A method as in claim 3 wherein step (a) is practiced at a cooling rate of between about 6° C./hr. to about 20° C./hr. and wherein the reference time interval associated with the cooling rate is about 3.5 minutes.

5. A method as in claim 3 wherein step (b) is practiced by means of a thermocouple.

6. A method as in claim 3 wherein step (c) is practiced by means of a temperature recorder.

7. An apparatus for determining the presence or absence of a pour point depressant additive in a hydrocarbon liquid comprising:

(a) cooling means for cooling a sample of the hydrocarbon liquid at a predetermined cooling rate from a temperature substantially above the cloud point temperature of the sample liquid to a temperature substantially below the cloud point temperature of the sample liquid;

(b) temperature sensing means for continuously sensing the temperature of the sample liquid while the sample liquid is cooled to establish a cooling rate curve for the sample liquid;

(c) means for determining points on the cooling rate curve at which a deflection of the curve begins and ends;

(d) means for determining the time interval between the beginning and ending points of the cooling rate curve deflection; and (e) means for comparing the determined time interval with a reference time interval associated with said predetermined cooling rate to establish whether the determined time interval is less than or greater than the reference time interval to respectively establish the presence or absence of a pour point depressant additive in the sample liquid.

8. An apparatus as in claim 7 wherein said cooling means cools the sample liquid at a cooling rate of between about 6° C./hr. to about 20° C./hr. and wherein the reference time interval associated with the cooling rate is about 3.5 minutes.

9. An apparatus as in claim 7 wherein said temperature sensing means include a thermocouple.

10. A method as in claim 7 wherein said temperature sensing means includes a temperature recorder.

11. Apparatus for determining the presence or absence of a pour point depressant additive in a hydrocarbon liquid comprising:

cooling means for cooling a sample of the hydrocarbon liquid at a predetermined cooling rate to derive a cooling rate curve for the hydrocarbon liquid;

means for determining a time interval between beginning and ending deflection points of the cooling rate curve; and comparator means for comparing said determined time interval to a reference time interval associated with said predetermined cooling rate to establish whether the determined time interval is less than or greater than said reference time interval thereby establishing the presence or absence, respectively, of a pour point depressant additive in the hydrocarbon liquid sample.

* * * * *